(12) United States Patent
Highnam et al.

(10) Patent No.: US 11,246,550 B2
(45) Date of Patent: Feb. 15, 2022

(54) METHOD FOR DETECTION AND QUANTIFICATION OF ARTERIAL CALCIFICATION

(71) Applicant: VOLPARA HEALTH TECHNOLOGIES LIMITED, Wellington (NZ)

(72) Inventors: Ralph Highnam, Wellington (NZ); Melissa Hill, Issy les Moulineaux (FR)

(73) Assignee: VOLPARA HEALTH TECHNOLOGIES LIMITED, Wellington (NZ)

(*) Notice: Subject to any disclaimer, the term of this patent is extended or adjusted under 35 U.S.C. 154(b) by 24 days.

(21) Appl. No.: 16/623,346

(22) PCT Filed: Jun. 18, 2018

(86) PCT No.: PCT/IB2018/054462
§ 371 (c)(1),
(2) Date: Dec. 16, 2019

(87) PCT Pub. No.: WO2018/229732
PCT Pub. Date: Dec. 20, 2018

(65) Prior Publication Data
US 2021/0145388 A1 May 20, 2021

(30) Foreign Application Priority Data

Jun. 16, 2017 (NZ) ........................................ 732921

(51) Int. Cl.
*G06K 9/00* (2006.01)
*A61B 6/00* (2006.01)
(Continued)

(52) U.S. Cl.
CPC ............ *A61B 6/502* (2013.01); *A61B 6/5217* (2013.01); *G06T 7/0012* (2013.01); *G06T 7/12* (2017.01);
(Continued)

(58) Field of Classification Search
CPC ....................................................... A61B 6/502
See application file for complete search history.

(56) References Cited

U.S. PATENT DOCUMENTS

2010/0215225 A1* 8/2010 Kadomura ................ G06T 7/62
382/128
2012/0189175 A1 7/2012 Highnam et al.
(Continued)

OTHER PUBLICATIONS

Jie-Zhi Cheng et al; Automated Delineation of Calcified Vessels in Mammography by Tracking with Uncertainty and Graphical Linking Techniques, IEEE Transactions on Medical Imaging; IEEE Service Center, Piscataway, NJ, US, vol. 31, No. 11; Nov. 1, 2012; pp. 2143-2155, XP011491178; ISSN: 0278-0062; DOI: 10,1109/TMI.2012.2215880.

*Primary Examiner* — Oneal R Mistry
(74) *Attorney, Agent, or Firm* — Holland & Hart LLP (57) ABSTRACT

Use of tissue composition and anthropomorphic measures in a method for the detection and quantification of arterial calcification in an organ is described for disease risk prediction and stratification. A radiographic image of an organ is transformed quantitatively to a tissue composition map indicating a total amount of organ tissue; a calcification map is generated indicating position in the tissue composition map of calcified tissue; calcification free tissue composition map is generated from the tissue composition map using the position of calcified tissue in the calcification map; a vessel map of the position of vessels in the tissue composition map is generated; and the vessel map is combined with the calcification map to generate a map of vessel calcification
(Continued)

indicating the position of calcified vessels in the tissue composition map. Scores are based on arterial calcification in a breast which indicates disease in the breast and other organs.

20 Claims, 3 Drawing Sheets

(51) Int. Cl.
*G06T 7/12* (2017.01)
*G16H 50/30* (2018.01)
*G06T 7/00* (2017.01)

(52) U.S. Cl.
CPC ... *G16H 50/30* (2018.01); *G06T 2207/30068* (2013.01); *G06T 2207/30101* (2013.01)

(56) References Cited

U.S. PATENT DOCUMENTS

| | | | |
|---|---|---|---|
| 2012/0238870 A1* | 9/2012 | Smith | A61B 6/502 |
| | | | 600/431 |
| 2014/0003701 A1 | 1/2014 | Masood et al. | |
| 2015/0141767 A1* | 5/2015 | Rogers | A61B 5/686 |
| | | | 600/301 |
| 2017/0337687 A1* | 11/2017 | Wang | G06T 7/11 |
| 2017/0367674 A1* | 12/2017 | Arai | A61B 6/42 |
| 2018/0068062 A1* | 3/2018 | Zhang | G16B 20/00 |
| 2018/0137244 A1* | 5/2018 | Sorenson | G16H 50/20 |

* cited by examiner

METHOD FOR DETECTION AND QUANTIFICATION OF ARTERIAL CALCIFICATION

CROSS REFERENCE TO RELATED APPLICATIONS

This application is a U.S. National Entry and claims priority to PCT International Patent Application No. PCT/IB2018/054462, filed Jun. 18, 2018, and entitled "METHOD FOR DETECTION AND QUANTIFICATION OF ARTERIAL CALCIFICATION", which claims priority to New Zealand Patent Application No. 732921, filed Jun. 16, 2017, the entire disclosures of which are incorporated herein by this reference.

FIELD OF THE INVENTION

The present invention relates to use of tissue composition and anthropomorphic measures in a method for the detection and quantification of arterial calcification for disease risk prediction and stratification. More specifically the method relates to breast tissue composition and arterial calcification in the breast. The invention also relates to scores based on arterial calcification in a breast which indicates disease in the breast and other organs.

BACKGROUND

Vascular calcification is defined as "inappropriate and pathological deposition of mineral in the form of calcium phosphate salts in the vascular tissues".

Calcification is restricted to the arteries and may occur in either the medial or intimal layer depending on the pathological process. In the intimal layer, calcification occurs in medium to large sized arteries. Calcification of the intima is usually associated with atherosclerosis and inflammation. Calcification of the medial layer, or Mönckeberg's sclerosis, occurs in arteries of any size. This form of calcification leads to increased vessel stiffness, hypertension, peripheral vascular disease, and altered coronary perfusion.

Mammography is a diagnostic and screening process where x-rays are used to examine the breast. It is primarily used for breast cancer detection. However, mammography can also reveal breast abnormalities including arterial calcifications.

PRIOR ART

There is known to be an association between arterial calcification and the risk of disease and mortality. The association of arterial calcification with risk of disease and mortality differs across various peripheral vascular beds. Calcification of arteries in the breast has been demonstrated to be associated with chronic kidney disease, bone mineral density reduction, diabetes mellitus, metabolic syndrome, hypertension, coronary artery disease, and stroke.

Examples of background information in the field include:
Margolies, M. Salvatore, H. S. Hecht, S. Kotkin, R. Yip, U. Baber, V. Bishay, J. Narula, D. Yankelevitz, and C. Henschke, "Digital mammography and screening for coronary artery disease," JACC Cardiovasc. Imaging, p. Online First, 2016;
F. Aziz, "Coronary artery disease in women: an unsolved dilemma," J. Clin. Med. Res., vol. 6, no. 2, pp. 86-90, April 2014;
C. Iribarren and S. Molloi, "Breast Arterial Calcification: a New Marker of Cardiovascular Risk?," Curr. Cardiovasc. Risk Rep., vol. 7, no. 2, pp. 126-135, April 2013;
S. Molloi, et al, "Quantification of breast arterial calcification using full field digital mammography," Med. Phys., vol. 35, no. 4, pp. 1428-39, 2008;
S. Molloi, T. Xu, J. Ducote, and C. Iribarren, "Quantification of breast arterial calcification using full field digital mammography," Med. Phys., vol. 35, no. 4, pp. 1428-39, 2008;
S. Molloi, T. Mehraien, C. Iribarren, C. Smith, J. L. Ducote, and S. A. Feig, "Reproducibility of Breast Arterial Calcium Mass Quantification Using Digital Mammography," Acad. Radiol., vol. 16, no. 3, pp. 275-282, 2009;
J. Ge, H. P. Chan, B. Sahiner, C. Zhou, M. A. Helvie, J. Wei, L. M. Hadjiiski, Y. Zhang, Y. T. Wu, and J. Shi, "Automated detection of breast vascular calcification on full-field digital mammograms," Med. Imaging 2008 Comput. Diagnosis, Pts 1 2, vol. 6915, p. 91517, 2008;
E. Nava and I. Barba, "Quantification of Vascular Calcifications on Digitized Mammograms," LNCS, vol. 6136, pp. 183-190, 2010;
J. Z. Cheng, E. B. Cole, E. D. Pisano, and D. Shen, "Detection of arterial calcification in mammograms by random walks," LNCS, vol. 5636, pp. 713-724, 2009;
J. Z. Cheng, C. M. Chen, E. B. Cole, E. D. Pisano, and D. Shen, "Automated delineation of calcified vessels in mammography by tracking with uncertainty and graphical linking techniques," IEEE Trans. Med. Imaging, vol. 31, no. 11, pp. 2143-2155, 2012;
J. Wang, H. Ding, F. Azamian, B. Zhou, C. Iribarren, S. Molloi, and P. Baldi, "Detecting Cardiovascular Disease from Mammograms with Deep Learning," IEEE Trans. Med. Imaging, pp. 1-1, 2017.
R. Highnam, J. Brady, N. Karssemeijer, M. Yaffe, "A Method and System for Analysing Tissue from Images", International Patent Application No. PCT/GB2010/001742.
R. Highnam, J. Brady, "A Method of Reconstruction of an Object from Projection Views", International Patent Application No. PCT/GB2014/000217.
M. Hill, R. Highnam, J. Marshall, D. Murray, L. Johnston, "System and Apparatus for Clinical Decision Optimisation", International Patent Application No. PCT/I B2017/054382.

Mammographically-identified breast arterial calcifications (BAC), have been shown on pathology to be entirely within the medial layer, giving an image appearance of continuous or intermittent parallel tracks, or linear tubular calcifications that are clearly associated with blood vessels.

Cardiovascular disease (CVD) is a leading cause of death for women among non-communicable diseases worldwide. Although women are typically underserved in screening for cardiovascular-related disease. A large proportion of cardiovascular events occur in women whose 10-year estimated risk of CVD is low, and thus guidelines would not routinely recommend therapy. Thus, alternative and complimentary methods of risk estimation are needed to identify women who might benefit from therapy.

Most prior clinical research correlating BAC with several cardiovascular disease (CVD) risk factors has relied on simple absence versus presence of BAC read from film-screen mammograms or on simplistic semi-quantitative BAC metrics with large uncertainty and standard deviation. Consequently, there have been inconsistent findings.

The problem of BAC physically masking the underlying breast tissues on an image has also not been specifically addressed.

A new approach is therefore required to achieve a significant advantage in predicting and stratifying risk, potentially for multiple diseases, ranging from cancer to CVD.

SUMMARY OF THE INVENTION

According to a first aspect of the present invention there is a method for detection and quantification of arterial calcification characterised in that a radiographic image is transformed quantitatively to a tissue composition map indicating a total amount of organ tissue; a calcification map is generated indicating position in the tissue composition map of calcified tissue; a calcification free tissue composition map is generated from the tissue composition map using the position of calcified tissue in the calcification map; a vessel map of the position of vessels in the tissue composition map is generated; and the vessel map is combined with the calcification map to generate a is map of vessel calcification indicating the position of calcified vessels in the tissue composition map.

Preferably a tissue composition map comprises quantitative values of total amount of organ tissue associated with respective quantitative values of position in the map. The other maps may similarly have quantitative values of calcified tissue, calcification free tissue, vessels, and calcified vessels at respective positions in the map.

Herein arterial calcification refers to calcification of blood vessels including booth veins and arteries.

Preferably a quantification measure of vessel calcification of the organ is generated from the vessel map. The location and/or quantity of vessel calcification may be used for disease risk prediction and stratification.

Preferably the organ is a breast. Preferably the method includes combining an anthropomorphic measurement of the breast with the map of vessel calcification for disease risk prediction and stratification.

Preferably the vessel map is generated from the tissue composition map using a segmentation algorithm.

Preferably the vessel segmentation algorithm is at least one or a combination of: an image filtration algorithm, a thresholding algorithm, an edge detection algorithm, or machine learning using supervised or unsupervised learning methods.

Preferably the tissue composition map is generated using spectral information from two or more x-ray energy ranges.

The calcification density and/or mass may thereby be measured using tissue composition information from the tissue composition map combined with the vessel map generated using the segmentation algorithm. Advantageously with the present method a quantitative amount of calcification density and/or mass may be determined. In the literature or prior art the term density may be used only in a qualitative fashion referring to opacity of vascular calcifications on a mammogram.

Preferably the calcification free tissue composition map includes values of a calcification-free tissue composition estimated by interpolation between values of the total amount of tissue that neighbours the vessel locations. Positions that are neighbours may be adjacent or within a preselected proximity preferably within one, two or three times the neighbour vessel width.

Preferably the vessel calcification is evaluated to generate a score of vessel calcification. The score may be an indicator of the health of the breast itself or BAC burden and/or a risk of disease in another body part or system.

Preferably a density of the organ is generated for indicating the total amounts of tissue in the tissue composition map.

Preferably the density of the organ is evaluated in combination with the vessel calcification to modify the score of vessel calcification or to generate a second score for correlation with risk of disease.

Preferably density of the organ is generated from the calcification free tissue composition map for indicating the total amounts of tissue after the calcification has been excluded from the tissue composition map. Advantageously a density unskewed by calcification may be generated from quantitative values of the total amount of tissue except for calcified tissue.

Preferably the density is the density of a breast and used for tissue functional status and/or disease risk prediction and stratification.

Advantageously the method is useful for generating a score to represent BAC burden. The score is preferably numerical. BAC burden is indicative of tissue functional status or health and/or disease risk prediction and stratification.

According to a second aspect of the invention there is a method for generating a score to represent BAC burden, comprising a quantitative analysis of calcified vessels in a map of vessel calcification in a breast, wherein one or more measures are used to obtain the score including:
i) counting the number of vessels with calcifications;
ii) measuring the length of segments of calcifications of the vessels;
iii) measuring the area of the segments of calcifications;
iv) measuring of the volume of the segments of calcifications; and/or
v) measuring the density or mass of the segments of calcifications.

Preferably at least one of the following anthropomorphic measures of the breast made from a tissue composition map is used to obtain the score including:
i) measuring breast volume;
ii) measuring fibroglandular tissue volume;
iii) measuring calcification-free breast tissue composition, preferably requiring a measure of the breast volume (e.g., volumetric breast density);
iv) measuring chest-wall-to-nipple distance (e.g., preferably from MLO view), and preferably requiring a means to identify the pectoralis muscle and the nipple;
v) measuring the total length of blood vessels including calcified and uncalcified vessels; and/or
vi) counting the blood vessels including calcified and uncalcified blood vessels.

Preferably measuring the breast volume includes requiring measurement of the projected breast area in a radiographic image, the breast thickness, a model for breast peripheral thickness, and a model for deformation of the breast positioning device.

Preferably measuring the chest-wall-to-nipple distance requires a means to identify the locations of features which are anatomical landmarks and to segment these features, which include the pectoralis muscle and the nipple. To segment these features, a segmentation algorithm may be used which is at least one or a combination of: an image filtration algorithm, a thresholding algorithm, an edge detection algorithm, or machine learning using supervised or unsupervised learning methods.

Preferably measuring the fibroglandular tissue volume includes requiring the measurement of the breast volume and measuring breast tissue composition by generating a tissue composition map.

Preferably the tissue composition map is obtained by quantitively transforming a radiographic image of an organ, preferably the breast.

Preferably the tissue composition map is a density map which may be a map of total breast tissue density at respective positions in the map.

Preferably the density or mass of the segments of calcifications is measured using composition of the tissue in the breast determined from a breast density map, or dual-energy, triple-energy or photon-counting image spectral information combined with a physics model of image acquisition.

Preferably measuring the volume of vessel calcifications requires measuring the breast thickness and using a model for deformation of a breast positioning device. Hence deformation of the breast position device itself is taken into account.

Among other features the present method preferably includes BAC detection and quantification that accounts for tissue composition. Hence the present method is novel over other methods that analyze image pixel values directly. Such other methods are limited by a lack of knowledge of tissue composition, and a technology dependence of the pixel values. The present method is also novel over other methods which convert to quantitative calcification values using calibrated data (look-up tables) where some assumptions about tissue composition must be made e.g., assumptions as to an average breast density.

The present method preferably includes use of the method of BAC detection and quantification to improve the accuracy of tissue quantification for the purposes of breast density measurement. Hence the present method is novel by use of a calcification map to make a soft-tissue composition map that excludes calcified tissue. Soft-tissue including adipose, fibroglandular, and skin tissue of for example a breast. Such a map may be used to calculate breast density and does have a better relationship with risk than if the calcifications were included which biases the density measure upwards.

The present method preferably includes BAC detection and quantification which is performed in a manner independent to the technology used for image acquisition. Other methods using the image pixel values directly have technology-dependent results. For example, other methods which convert to calcification quantities only work with photon-counting systems. The present method may be a technology-independent method.

In the application of BAC analysis, the term 'density' has been used in a qualitative fashion, referring to the relative appearance of the opacity of vascular calcifications on a mammogram. With the present method density is also determined quantitatively.

The present method preferably includes quantification of breast anthropomorphic features alongside BAC to provide complementary information for generating a quantitative score for the estimation of a BAC burden. Other methods do not quantify breast anthropomorphic features and combine with quantified BAC to estimate a BAC burden score.

The present method preferably includes use of quantitative BAC measures and anthropomorphic features for risk stratification for a variety of diseases. Advantageously use of breast anthropomorphic features improves risk stratification over that based on BAC only.

The present method preferably includes use of a BAC score and/or BAC-related risk estimation, including anthropomorphic features to inform patient clinical management. The present method is advantageous over other methods by using this information for clinical management of breast imaging itself.

The invention will now be described, by way of example only, with reference to the accompanying drawings in which:

BRIEF DESCRIPTION OF THE FIGURES

FIG. 1(a) shows a sample mammogram of a human breast as it would normally be displayed to a radiologist;

FIG. 1(b) is a magnified region from the image in FIG. 1(a) showing a calcified blood vessel;

FIG. 1(c) illustrates a tissue composition map with calcifications included for the mammogram in (a). The colour bar represents fibroglandular tissue thickness in mm.

FIG. 1(d) illustrates a tissue composition map after calcifications have been removed for the mammogram in (a). The colour bar represents fibroglandular tissue thickness in mm.

FIG. 1(e) shows an example map of BAC locations for the mammogram in (a).

FIG. 1(f) illustrates an example of BAC identification, with the identified BAC delineated in red, overlaying the mammogram from (a).

DETAILED DESCRIPTION OF THE INVENTION

Herein are disclosed particulars of a method for the detection and quantification of breast arterial calcification, which uses information relating to tissue composition, breast anthropomorphic measures, and the application of these measurements as biomarkers for the prediction and stratification of risk of disease.

Figure 1:
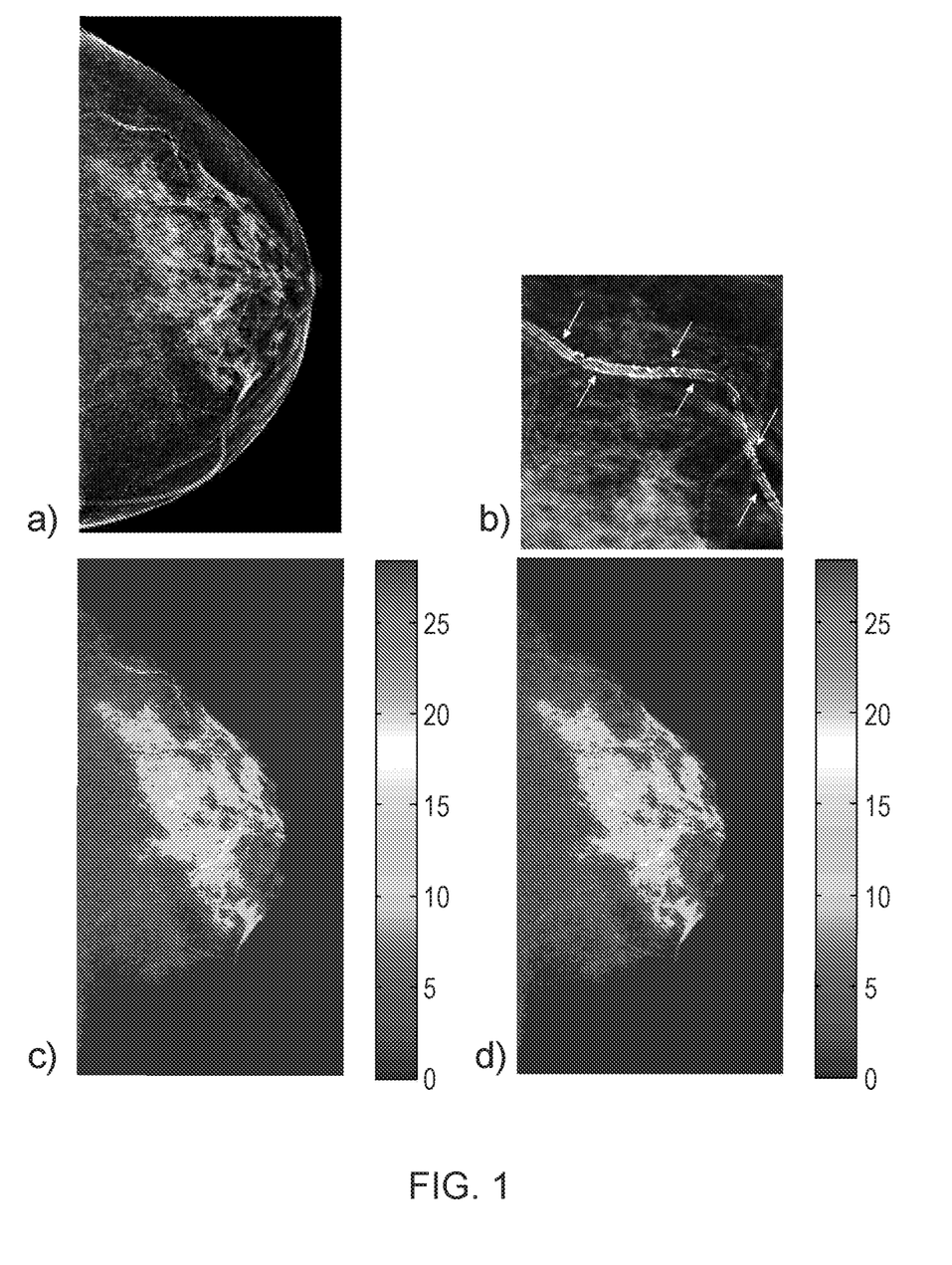
FIG. 1 illustrates a typical presentation of BAC in a mammogram and an example of BAC identification.

In an illustrative embodiment such as shown in FIG. 1, there is shown a mammogram which is a radiographic image of a breast. The radiographic image is transformed quantitatively to a tissue composition map.

The tissue composition map comprises a total amount of tissue in the breast associated with positions in the map. The tissue composition map may be illustrated by a height or a colour for each total amount of tissue for clear visualization. The positions and total amounts are also numerical quantities and may also be recorded or stored electronically for processing.

Figure 2:
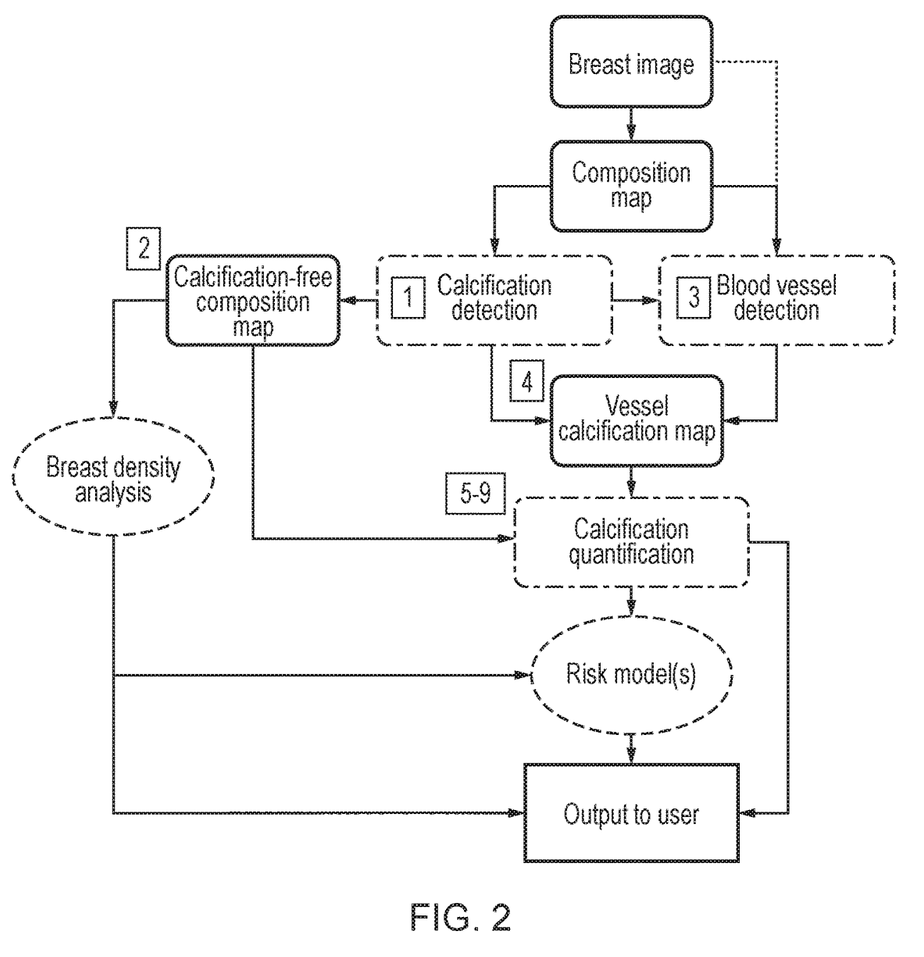
FIG. 2 illustrates an illustrative embodiment of BAC detection, quantification and risk estimation and the input and output of data.

In an illustrative embodiment such as shown in FIG. 2, calcified arterial vessels are identified in a breast image and:

1. the tissue composition map is generated, using, for example Volpara®Density, and the tissue composition map is used to identify calcifications, and the 'height' of materials at the locations of the calcifications.

As defined here, the 'height' refers to a value in the tissue composition map that represents the amount of non-adipose material (i.e. fibroglandular material and calcification) at that location. Advantageously height may be visualized on a three axis view of the map. In the case where a calcification is present, the height in the tissue composition map will include a quantity related to the thickness of glandular and fibrous breast tissues, plus a height related to the calcification thickness.

In some cases, the height at the calcification location(s) will be greater than the patient organ (i.e. breast) thickness. In such cases, the non-physical heights are an indicator of the presence of calcifications. In other cases, or in other locations, the height of the tissue and calcification combined will be less than the patient organ thickness. In such cases, a combination of edge-detection and calcification morphology information can be used to distinguish calcifications from soft tissues (e.g., adipose, fibroglandular, and skin). The calcification segmentation algorithm is at least one or a combination of: an image filtration algorithm, a thresholding algorithm, an edge detection algorithm, or machine learning using supervised or unsupervised learning methods. So a quantitative value for calcified tissue at these locations is determinable. The locations of the candidate calcifications in the breast image are stored.

2. The locations of the calcifications identified in step 1 are used to remove the 'height' of calcifications from tissue composition values. Interpolated tissue composition values from map locations that neighbour calcifications are used to 'replace' the confounded tissue composition information at the calcification locations. A 'calcification-free' tissue composition map is generated. This map is used for further steps in the BAC analysis method, but can also be used for breast density analysis, where it is desirable to exclude calcifications from breast tissue composition measures.

The present method overcomes the problem of BAC physically masking the underlying breast tissues on an image, and their removal for tissue composition measurement. The present method is an effective method to identify BAC so that it can be excluded from breast density estimates, and to additionally estimate the tissue composition masked by the BAC.

The present method is a reliable and accurate automated measure of BAC which comprises reference to tissue composition and provides a significant advantage in predicting and stratifying risk, potentially for multiple diseases, ranging from the breast itself to other organs.

3. A vessel segmentation algorithm is applied to the tissue composition map or breast image. The segmentation algorithm identifies objects in the tissue composition map such as a vessel based on the object morphology. The search is constrained as necessary using blood vessel anatomical information, for example, vessels that originate from the chest wall; (i.e., to avoid ducts); and vessels with diameters in a range of interest: e.g., 0.4 to 3 mm diameter as they enter the breast at the chest wall. In the preferred embodiment, the vessel segmentation algorithm is applied to the tissue composition map so that the analysis is not affected by the image acquisition technology and implementation.

The tissue composition map includes total amounts of tissue which are specific to the breast. The radiographic mammogram includes pixel values which are specific to the breast and the radiograph apparatus used to obtain the mammogram.

Use of the segmentation algorithm together with the tissue composition map allows for objective search and location of vessels in the tissue composition map independent of various radiograph apparatus. The vessels located by the segmentation algorithm may be referred to as segmented vessels.

In another embodiment, at step 1, and/or 3, multiple views of the breast are used to improve the confidence in vessel and/or calcification location.

4. The segmented vessels that contain calcifications are detected as the intersection of the vessel locations and the calcification locations from steps 1 and 3. A BAC map is created that can be output for visual interpretation by the user. A report, flagging the presence of BAC in the breast image, may also be communicated to the user.

The vessel segmentation, or detection, algorithm at step 3, use anys one of, or a combination of, previously described algorithms, such as image filtration, thresholding, or edge detection. For example, in one embodiment, machine learning, using either supervised, or unsupervised learning methods are applied to the tissue composition map for BAC identification. Note that transformation of raw image pixel intensities to tissue compositions, presents a technology-neutral scale from which the BAC detection and quantification can be made. Thus, the use in the present method of the tissue composition map together with the calcification and vessel segmentation algorithms overcomes the technology-dependence of BAC identification using classical methods for calcification and vessel detection, including the more recent machine learning algorithms.

Image thresholding by the vessel segmentation or detection algorithm is by combination with a means to detect edges and/or curvilinear structures due to breast tissue complexity. An advantage is superior accuracy operating on a tissue composition map compared to native image pixel data. By removing the technology-dependence of the image intensities, a tissue composition map has a direct relationship with the true patient anatomy. Thus, the threshold values are specific to patient anatomy.

Image filtration and edge detection both have substantially superior accuracy operating on tissue composition maps compared to 'For Presentation' images. The 'For Presentation' format has manufacturer-specific processing applied, which can include non-linear transformations that interfere with a relationship between tissue properties and the image pixel values. Operating on 'For Processing' images keeps this relationship is intact, but the pixel values are still technology-dependent and are dependent on patient organ thickness. Using tissue composition maps instead of 'For Processing' images comparatively reduces the dependence on organ thickness, and permits superior accuracy using these methods.

Machine learning also benefits from the use of tissue composition maps, especially compared to applying machine learning to 'For Presentation' images which vary due to idiosyncrasies of the apparatus and image dress up techniques used to generate the 'For Presentation' images. Machine learning is applicable to vessel segmentation and detection to quantify BAC.

Advantageously severity of BAC is described on continuous quantitative scale. Arteries with high calcium deposition may indicate advanced or severe disease compared to cases with minimal calcification.

Advantageously with the method it is possible to quantitatively score BAC using measures that are not limited to the number of vessels with calcium deposition, involved vessel length, calcified vessel diameter, and calcification density, or mass.

Advantageously the method accounts for breast density and so overcome the problem that although calcium has a relatively high x-ray attenuation compared to soft tissues, the size, shape and contrast of BAC is variable against a background of breast parenchyma that is highly subject-dependent, both in terms of physical tissue pattern, and in terms of tissue composition, which is sometimes quantified by a woman's breast density.

Since the method generates a tissue composition map including various tissues in the breast, it is possible to distinguish between calcified arteries and other calcifications within the breast.

Since the calcifications are detected from numerical quantities independent of apparatus, accurate and objective values for the calcified tissue are obtained.

The method is therefore an improvement over that of Molloi et al., which performs semi-automated BAC quantification, but is hampered by a requirement for careful and periodic calibration of the image acquisition device using phantom materials. Furthermore, the Molloi approach uses manual calcification identification, and has a large uncertainty, with a standard deviation of calcium measurement of 10 to 50% due to variability in breast density.

The present method is also an improvement over a method by Ge et al. to identify arterial calcifications using parameters tuned according to image intensity. The method of Ge et al is limited for calcified vessel morphology quantification, does not permit measurement of calcification density, and does not account for tissue composition.

The present method is also an improvement over a method by Nava et al. who proposed a BAC identification method comprised of multiple steps, including edge detection and thresholding of image pixels, thus operating on technology-dependent image properties, and thereby limiting the scope of applicability unless the method is tuned for each system type. The Nava et al. quantification metric is also simplistic and without reference to morphology or tissue composition, being based on only the number of image pixels with calcification.

The present method is also an improvement over a method by Cheng et al. who also developed a method to identify arterial calcifications, with improved calcified vessel morphology quantification compared to the Ge et al. approach, but this method is also impaired by local variations of tissue composition and its quantification is limited to morphology metrics.

The present method is also an improvement over method by Wang et al. that uses a neural network for BAC detection, which employs unsupervised learning, and combines this with the Molloi et al. method for BAC quantification. The method of Wang et al does not address the limitations of either the technology-dependence of machine learning as applied to mammogram pixel values, or the limited accuracy of BAC quantification as a function of breast density.

In a further embodiment, the present invention comprises the development of a score to represent patient BAC burden. This score comprises quantitative analysis of calcified vessels in the BAC map (Step 4) for use as metrics of BAC burden that can be important in risk assessment, whereby:

5. the number of vessels with calcifications are counted. For example, by counting the number of segmented blood vessels with one or more calcifications present within segments of a continuous vessel; and 6. the length of the calcified vessel segments is measured. For example, as the longest dimension along a calcification within a given vessel; and 7. the area of the vessel calcifications is measured. For example, as the two-dimensional area of each calcification in the tissue composition map; and 8. the volume of vessel calcifications is measured. For example, using the calcification thickness and the area measured in step 7, the volume is computed, where the calcification thickness is determined as the difference between the overall breast thickness at the given calcification location and the thickness of soft tissues (e.g., adipose, fibroglandular, and skin) at the calcification location. To determine breast thickness a model is used for deformation of the breast positioning device due to potential for tilt/warp, resulting in different thickness according to location.

9. the calcification density, or mass is measured; using tissue composition information (e.g., from a breast density image, or dual-energy, triple-energy or photon-counting image spectral information) and a vessel segmentation map combined with a physics model of image acquisition. Hence a quantitative value of calcification density is obtained. In the application of BAC analysis, the term 'density' has been used in a qualitative fashion, referring to the relative appearance of the opacity of vascular calcifications on a mammogram.

9a. the vessel map generated with a segmentation algorithm is used in combination with reference vessel diameters (i.e., typical breast vessel diameters known from the literature), the calcification map, and the areas of each BAC from step 7 to estimate the proportion of each involved vessel that is calcified. For example, if the total projected area of a vessel has calcification, it would be reported that the entire involved vessel segment has calcification. This information is further refined to reflect BAC severity by estimating the proportion of occluded lumen by comparing the BAC thickness from the calcification map to the vessel diameter estimated from the vessel segmentation map. The result can be reported as the percentage (%) of vessel lumen occluded by calcification.

9b. In a simplified version of step 9a, the volume of calcification from step 8 can be compared to the estimated vessel volume of the involved segment. This measure would not directly comprise information about the calcification status of each vessel wall (e.g, as in step 9a), but this measure would nonetheless reflect the percentage (%) of vessel lumen occluded by calcification.

9c. In a further simplified implementation, the calcification density (g/cm3) of each involved BAC segment is calculated as the mass of calcification in the segment, divided by the estimated involved vessel segment volume. The calcification mass in grams is first determined as the density of calcification (i.e., the density in g/cm3 from the literature of a solid unit of calcification with the typical chemical composition) multiplied by the volume of BAC as determined in step 8. Next, the density of this calcification within the vessel is calculated as the BAC mass divided by the total volume of the involved vessel segment. Note that involved vessel volume would only equal the BAC volume if the entire vessel is occluded by calcification. Thus, this measure of calcification density reflects the proportion of occluded vessel lumen indirectly, and represents an averaged measure over the length of the vessel segment with BAC.

9d. In the simplest form, the calcification mass (e.g., grams, as computed in step 9c) can be computed for each BAC, and used as information to describe individual BAC directly, or can be combined as a total mass of BAC for each breast.

The metrics described in 5 to 9 can be combined to determine a BAC 'score' representing the extent of disease, or the burden of disease in the patient.

Advantages are gained in risk prediction by collecting data on the length of all calcified vessel segments.

A multivariate model for BAC burden is also a novel development that takes in all of the measures from 5 to 9, and combines the measures based on a model learned from a training data set.

In one embodiment, when spectral information is available from two or more energy ranges, such as from a photon-counting system, or from dual- or triple-energy imaging, the composition of soft breast tissues and calcifications is simultaneously quantified. The tissue composition map generated at step 1, is produced by material decomposition, using one of several methods, such as energy-weighting, polynomial fitting, or statistical methods, such as maximum likelihood to estimate composition. Superior accuracy of calcification quantification is achieved by using two or more energy thresholds in photon counting systems, or triple-energy imaging, compared to the previously described dual-energy methods, or photon-counting using one energy threshold.

In step 2, the 'local' calcification-free tissue composition can be estimated by interpolation between map values that neighbour the blood vessel in the tissue composition map. Interpolation could be performed using several different methods. This procedure effectively removes the calcification from the tissue composition map, such that the remaining 'height' of the tissue composition map value relates to soft breast tissues only. Thus, a new calcification-free tissue composition map is created in which an estimated tissue composition is 'filled' into regions that belong to calcifications. The calcification density is estimated using the x-ray beam quality information, calcification chemical composition, and the calcification height compared to the remaining estimated local calcification-free tissue.

In addition to the quantification of BAC (steps 5 to 9), patient anthropomorphic measures are made from the tissue composition map for their inclusion in a BAC burden score.

Advantageously the score furthers BAC risk stratification by the inclusion of anthropomorphic features that describe measures of a patient body habitus. Typical anthropomorphic measures include height, bodyweight and waist circumference. Also, breast-specific measurements such as breast volume, fibroglandular tissue volume, breast tissue composition, and surrogates for chest-wall-to-nipple length, such as the posterior nipple line as measured from a mammogram, help to improve the specificity of BAC risk estimation by accounting for patient-specific anatomy.

Figure 3:
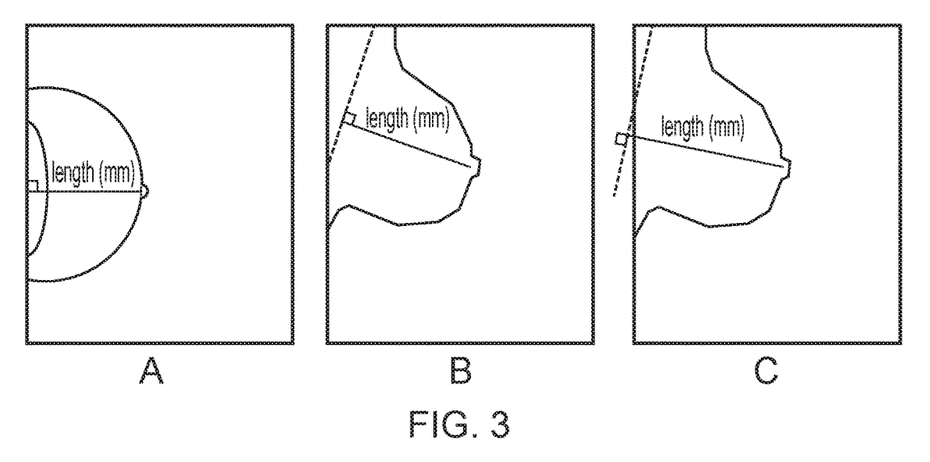
FIG. 3 demonstrates an illustrative embodiment of the measurement of an example breast anthropomorphic measure.

Measurement of the posterior nipple line is shown in FIG. 3 for three different positioning cases, (A) in the craniocaudal view with good positioning; (B) in the mediolateral oblique (MLO) view with good positioning, and (C) in the MLO view when the pectoral muscle is not adequately extended.

Anthropomorphic measures of the breast made from the tissue composition map include:

10. breast volume; requiring measurement of the projected breast area, the compressed breast thickness, a model for breast peripheral thickness, and a model for deformation of the breast compression device as described in international application PCT/GB2010/001742; and 11. fibroglandular tissue volume; requiring the breast volume from step 10, along with the breast tissue composition which may be obtained from the tissue composition map itself, e.g., density map, as described in international application PCT/GB2014/000217; and 12. breast tissue composition (e.g., volumetric breast density); requiring the breast volume (step 10) and the tissue composition which may be obtained from the tissue composition map itself, e.g., density map; and 13. chest-wall-to-nipple distance (e.g., from MLO view); requiring a means to identify the pectoralis muscle and the nipple as described in international application PCT/162017/054382.

The quantitative BAC and breast morphology measures are used independently, or combined in a multi-parametric model to develop a single score of BAC burden that accounts for patient breast characteristics as well as calcified vessel characteristics.

Multi-parametric modelling is done by means of an approach such as logistic regression, or by using machine-learning algorithms to optimize the value of the score for risk prediction. In the former case, an example implementation would require input, per breast, of the BAC measures introduced in 5 to 9 into a multi-parametric model, while at the same time the anthropomorphic organ measures in steps 10 to 13 are also input to the same model, per breast. The model output is an ordinal score of patient BAC burden, that includes consideration for both BAC characteristics and organ characteristics.

It is thus a feature of the present method that the association between BAC quantification variables, including its severity or burden, and breast anthropomorphic features such as volume and chest-wall-to-nipple distance are included as these and other such biomarkers are likely to be related to, and predictive of BAC quantitative measures for an individual. For example, a large chest-wall-to-nipple distance and large total volume, is correlated to longer calcified vessel lengths and greater number of involved vessels compared to similar measures in a small breast. Greater overall vascularity is required for large compared to small breasts, while on a local scale, the tissue in each breast has a similar level of perfusion. The present method incorporates quantitative and assured measurement of these characteristics which are otherwise laborious, variable and dependent on skill of clinician to measure. This empowers these characteristics relationships with BAC quantification and allow for the normalization of and refinement of BAC burden scores based on these characteristics.

Thus, in an embodiment, quantitative BAC measures are ordered, and/or scored and/or grouped into categories that relate to breast anthropomorphic measures. Grouping the BAC measures described in step 5 to 9 within categories for one or more of the anthropomorphic measures in step 10 to 13 allows for superior prediction of risk of disease compared to the use of the BAC measures in isolation. For example, grouping BAC measures according to total breast volume (e.g., small, medium, large) and breast composition (e.g., four density categories) stratifies women into appropriate risk categories.

In another embodiment, BAC estimates are normalized based on any one of several, or by a group of breast anthropomorphic measures. For example, the BAC measures described in step 5 and 6 are divided by the total breast volume described in 10 (or the fibroglandular tissue volume defined in 11) to account for patient breast size.

Similarly, the BAC lengths specified in step 6 is divided by the chest wall-to-nipple distance described in step 13, which does account for the longest potential vessel length in the patient breast according to the given mammographic positioning of the breast.

In another embodiment, the quantitative BAC and/or breast density results are ordered, and/or scored and/or grouped into categories that relate to risk of disease. These results are then reported for each patient. For example, the continuous measure of breast composition with calcifications excluded is grouped into one of four breast density categories according to thresholds that relate to risk of breast cancer. Similarly, the BAC measures in step 5 to 9, with or without grouping or normalization according to anthropomorphic measures step 10 to 13 is categorized according to their association with risk of CVD.

In a further embodiment, the results of BAC and anthropomorphic features quantitative analysis are input into risk models of disease to prepare a patient risk profile. Among other conditions, this includes risk relating to at least one of coronary artery disease, hypertension, metabolic syndrome, diabetes, osteoporosis, and breast cancer. The input to risk models is one of, or a combination of, individual 'raw' measures (i.e., BAC measures step 5 to 9, and/or anthropomorphic measures 10 to 13), normalized measures (i.e., BAC measures 5 to 9 scaled according to anthropomorphic measures 10 to 13), grouped measures (i.e., BAC measures step 5 to 9 grouped according to anthropomorphic measures step 10 to 13), or a BAC burden score.

In a further embodiment, patient data on BAC burden, including a BAC score, anthropomorphic features, and the related risk profile for disease(s) is used to determine patient management for various clinical decisions. Patient management decisions include, but are not limited to:
i) patient triage to appropriate imaging modalities for screening or diagnosis. A specific example is the potential contraindication for MRI using contrast agents due to renal insufficiency; and
ii) patient referral to a specialist health-care provider for indicated conditions; and iii) diagnostic work-up to test for the presence of one or more diseases suggested by a heighted risk, such as coronary artery disease (BAC burden), hypertension (BAC burden), metabolic syndrome (BAC burden), diabetes (BAC burden), osteoporosis (BAC burden), and breast cancer (breast density); and
iv) suggestion of lifestyle modifications to prevent or manage diseases for which the patient is at high risk; and
v) prescription of appropriate therapies to treat or prevent conditions for which the patient is at high-risk, or has confirmed, related to a heightened BAC burden; and
vi) appropriate patient surveillance for at-risk disease(s).

The invention has been described by way of examples only. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the claims.

The invention claimed is:

1. A method for detection and quantification of arterial calcification wherein:
- a radiographic image of an organ is transformed quantitatively to a tissue composition map indicating a total amount of organ tissue;
- a calcification map is generated indicating position in the tissue composition map of calcified tissue;
- a density map of the organ is generated from the calcification free tissue composition map;
- a calcification free tissue composition map is generated from the tissue composition map using the position of calcified tissue in the calcification map;
- a vessel map of the position of vessels in the tissue composition map is generated; and
- the vessel map is combined with the calcification map and density map generated from the calcification free tissue composition map to generate a map of vessel calcification indicating position and quantification of calcification of calcified vessels in the tissue composition map.

2. The method according to claim 1, wherein a quantification measure of vessel calcification of the organ is generated from the vessel map for disease risk prediction and stratification.

3. The method according to claim 1, wherein the organ is a breast including combining an anthropomorphic measurement of the breast with the map of vessel calcification for disease risk prediction and stratification.

4. The method according to claim 2, wherein the organ is a breast including combining an anthropomorphic measurement of the breast with the quantitative measure of vessel calcification for disease risk prediction and stratification.

5. The method according to claim 1, wherein the vessel map is generated from the tissue composition map using a segmentation algorithm.

6. The method according to claim 5, wherein the vessel segmentation algorithm is at least one or a combination of: an image filtration algorithm, a thresholding algorithm, an edge detection algorithm, or machine learning using supervised or unsupervised learning methods.

7. The method according to claim 1, including generating the tissue map using spectral information from two or more energy ranges.

8. The method according to claim 1, wherein the calcification free tissue composition map includes values of a calcification-free tissue composition estimated by interpolation between values of the total amount of tissue that neighbors the vessel locations.

9. The method according to any preceding claim 1, including evaluating the vessel calcification to generate a score of vessel calcification.

10. The method according to claim 1, wherein the density is the density of a breast and used for tissue functional status and/or disease risk prediction and stratification.

11. The method according to claim 1, including evaluating the density of the organ generated from the calcification free tissue composition map in combination with the vessel calcification and to modify the score of vessel calcification for correlation with risk of disease.

12. A method for generating a score to represent BAC burden, the method comprising:
- a calcification map is generated indicating position of calcification in a tissue composition map of breast;
- a calcification free tissue composition map is generated from the tissue composition map using the position of calcified tissue in the calcification map;
- a density map of the breast is generated from the calcification free tissue composition map;
- a vessel map of the position of vessels in the tissue composition map is generated; and
- wherein the vessel map is combined with the calcification map and density map generated from the calcification free tissue composition map to generate in a map of vessel calcification in the breast, and one or more measures are used to obtain the score to represent the BAC burden including:
  i) counting the number of vessels with calcifications;
  ii) measuring the length of segments of calcifications of the vessels;
  iii) measuring the area of the segments of calcifications;
  iv) measuring of the volume of the segments of calcifications;
  v) measuring the density or mass of the segments of calcifications.

13. The method according to claim 12, wherein at least one of the following anthropomorphic measures of the breast made from a tissue composition map is used to obtain the score including:
   i) measuring breast volume;
   ii) measuring fibroglandular tissue volume;
   iii) measuring calcification-free breast tissue composition;
   iv) measuring chest-wall-to-nipple distance;
   v) measuring the total length of blood vessels including calcified and uncalcified vessels;
   vi) counting the blood vessels including calcified and uncalcified blood vessels.

14. The method according to claim 13, wherein measuring the breast volume includes requiring measurement of the projected breast area in a radiographic image, the breast thickness, a model for breast peripheral thickness, and a model for deformation of a breast positioning device.

15. The method according to claim 13, wherein measuring the chest-wall-to-nipple distance requires a means to identify the locations of features which are anatomical landmarks and to segment these features which include the pectoralis muscle and the nipple.

16. The method according to claim 13, wherein measuring the fibroglandular tissue volume includes requiring the measurement of the breast volume and measuring breast tissue composition by generating a tissue composition map.

17. The method according to claim 12, wherein the density or mass of the segments of calcifications is measured using composition of the tissue in the breast determined from a breast density map.

18. The method according to claim 12, wherein the density or mass of the segments of calcifications is measured using composition of the tissue in the breast determined from a dual-energy, triple-energy or photon-counting image spectral with information combined with a physics model of image acquisition.

19. The method according to claim 12, wherein measuring the volume of vessel calcifications requires measuring the breast thickness and using a model for deformation of a breast positioning device.

20. A map of vessel calcification stored in a digital medium or visual image medium, wherein the map of vessel calcification is obtained according to the method of claim 1.

* * * * *